US010408793B2

(12) United States Patent
Capoglu et al.

(10) Patent No.: US 10,408,793 B2
(45) Date of Patent: Sep. 10, 2019

(54) MINIMIZING AZIMUTHAL CURRENT INDUCED ON TUBULARS BY TRANSMITTERS

(71) Applicant: Halliburton Energy Services, Inc., Houston, TX (US)

(72) Inventors: Ilker R. Capoglu, Houston, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 13 days.

(21) Appl. No.: 15/524,080

(22) PCT Filed: Apr. 21, 2016

(86) PCT No.: PCT/US2016/028679
§ 371 (c)(1),
(2) Date: May 3, 2017

(87) PCT Pub. No.: WO2017/184154
PCT Pub. Date: Oct. 26, 2017

(65) Prior Publication Data
US 2018/0196006 A1 Jul. 12, 2018

(51) Int. Cl.
*G01N 27/90* (2006.01)
*G01V 3/28* (2006.01)
(Continued)

(52) U.S. Cl.
CPC ......... *G01N 27/90* (2013.01); *E21B 47/0006* (2013.01); *G01N 33/24* (2013.01); *G01V 3/28* (2013.01)

(58) Field of Classification Search
CPC ... G01V 3/30; G01V 3/28; H01Q 1/04; G01N 27/90; G01N 33/24; E21B 47/011; E21B 47/01; E21B 47/0006
See application file for complete search history.

(56) References Cited

U.S. PATENT DOCUMENTS

| 5,396,175 A | 3/1995 | Seeman |
| 5,749,605 A | 5/1998 | Hampton et al. |

(Continued)

FOREIGN PATENT DOCUMENTS

WO 2014163707 10/2014

OTHER PUBLICATIONS

International Search Report and Written Opinion for Application No. PCT/US2016/028679 dated Mar. 29, 2017.

*Primary Examiner* — Jermele M Hollington
*Assistant Examiner* — Suresh K Rajaputra
(74) *Attorney, Agent, or Firm* — Jason Sedano; C. Tumey Law Group PLLC

(57) ABSTRACT

A tool and method for reducing azimuthal current. An EM induction tool may comprise a tubular, which may further comprise a body with a central axis and an insulating layer that may be non-azimuthally symmetric with respect to the central axis. The EM induction tool may further comprise a transmitter coupled to the tubular and a receiver coupled to the tubular. A method of reducing azimuthal current may comprise introducing a current through a transmitter into a subterranean formation, wherein the transmitter is coupled to a tubular, allowing an insulating layer of the tubular to at least partially block azimuthal currents originating from the transmitter from flowing on the tubular, wherein the insulating layer is non-azimuthally symmetric, and measuring eddy currents induced by the current with one or more receiver coupled to the tubular.

22 Claims, 13 Drawing Sheets

(51) Int. Cl.
*E21B 47/00* (2012.01)
*G01N 33/24* (2006.01)

(56) References Cited

U.S. PATENT DOCUMENTS

| | | | |
|---|---|---|---|
| 6,710,600 B1 * | 3/2004 | Kopecki | E21B 47/01 175/320 |
| 6,926,098 B2 | 8/2005 | Peter | |
| 8,154,420 B2 | 4/2012 | Petrovic et al. | |
| 8,171,613 B2 | 5/2012 | Reynolds, Jr. | |
| 8,844,648 B2 | 9/2014 | Bittar et al. | |
| 9,000,940 B2 | 4/2015 | Chau et al. | |
| 2002/0079899 A1 * | 6/2002 | Frey | E21B 43/086 324/338 |
| 2003/0155924 A1 | 8/2003 | Rosthal et al. | |
| 2015/0091577 A1 | 4/2015 | Donderici et al. | |
| 2015/0268371 A1 | 9/2015 | Donderici et al. | |

\* cited by examiner

MINIMIZING AZIMUTHAL CURRENT INDUCED ON TUBULARS BY TRANSMITTERS

BACKGROUND

The present disclosure relates to downhole electromagnetic induction tools and, more particularly, to apparatus and methods for electrically insulating an electromagnetic ("EM") induction tool to minimize azimuthal current induced by a transmitter on tubulars of the induction tool. As disclosed herein, the term "electromagnetic induction tool" may denote any electromagnetic tool which works at least in part based on induction principles. The term "electromagnetic induction tool" is not intended to limit the application to subterranean formation resistivity measurement and specifically includes ranging applications, where a distance and/or direction to a second wellbore may be calculated.

In well operations, it may be desirable to survey the formation using a downhole tool disposed in the wellbore. One type of downhole tool is an EM induction tool that may be used to make measurements of the electrical resistivity of earth formations penetrated by a wellbore or make measurements of distance and direction to a second well. EM induction tools may be used in logging-while-drilling/measuring-while-drilling operations, electromagnetic ranging, wireline logging, and permanent monitoring systems, among others. EM induction tools, or instruments, may typically comprise at least one transmitter and at least one receiver. The transmitter(s) and receiver(s) may be disposed on a tubular, such as a bottomhole assembly, mandrel, or casing joint. The EM induction tool may be implemented to determine the distance and direction to surrounding wells. Additionally, the EM induction tool may be disposed in a wellbore for the purpose of investigating electrical properties of subterranean formations and wells adjacent the wellbore. An electrical property of interest may be the electrical conductivity of particular portions of the formation. An alternating current having at least one frequency may be conducted through the transmitter(s). The alternating current may induce eddy current to flow within the surrounding subterranean formations or in adjacent well casings. This eddy current in turn may induce voltages in the receiver(s).

However, depending on the application, azimuthal currents could be flowing on the tubular associated with the EM induction tool. These azimuthal currents may constitute a significant portion of the direct signal at the receiver(s). The "direct signal" may be considered the signal recorded at the receiver(s) without any target present. The target may be a second wellbore, formation inhomogeneity, a bed boundary or an approaching water/carbon dioxide front. Thus, the direct signal would be present at the receiver(s) even in a homogenous formation. It is often desirable to minimize, reject, our process out the direct signal, as the direct signal may be very large compared to the target signal. Detecting the target signal in the presence of the direct signal often requires large dynamic range, which may be difficult to obtain in downhole electronics.

Currently, "gap sub" structures may be used for blocking axial currents on a downhole device. Gap sub structures may operate within galvanic application in which electrodes may create downhole device currents flowing primarily in the axial direction of the downhole device. However, there is a need to provide devices and methods for mitigating azimuthal current created within a downhole device by the transmitter. Characteristics of azimuthal current may be significantly different from axial currents that may be created by electrodes.

BRIEF DESCRIPTION OF THE DRAWINGS

These drawings illustrate certain aspects of some of the examples of the present invention, and should not be used to limit or define the invention.

DETAILED DESCRIPTION

The present disclosure relates generally to a device and method for mitigating azimuthal currents permeating a downhole device. More particularly, the disclosure may relate to downhole EM induction tools that may be insulated to mitigate azimuthal currents. The EM induction tools may be used in a number of downhole operations, including, without limitation, logging-while-drilling and/or measuring-while-drilling operations, electromagnetic ranging, wireline logging, and/or permanent monitoring systems. In examples, an insulated tubular may be provided to help prevent direct coupling between transmitters and/or receivers caused by current flowing along the azimuth of the insulated tubular.

Figure 1:
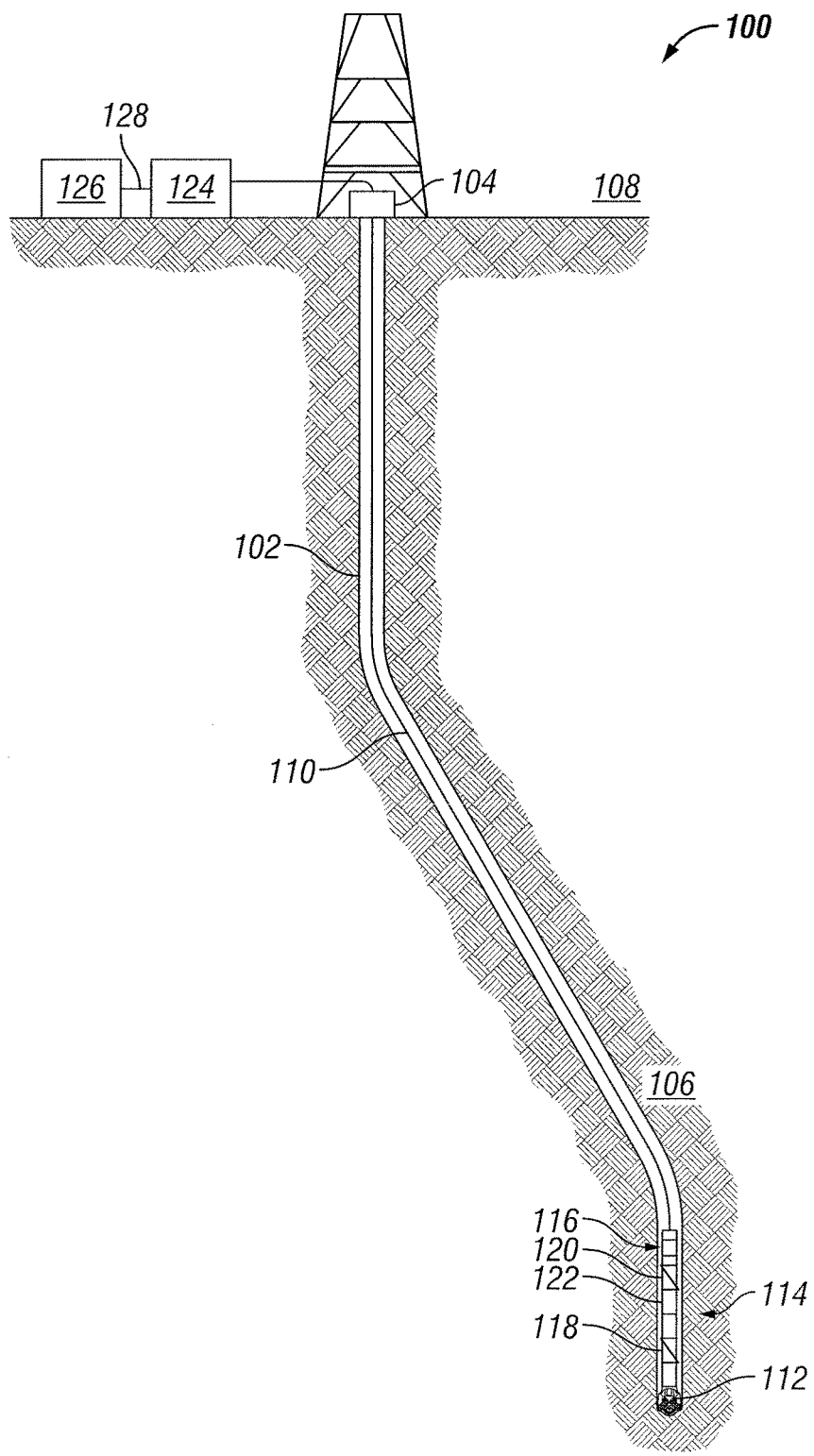
FIG. 1 is an example of a drilling system that includes an EM induction tool.

FIG. 1 illustrates an example of a drilling system 100. As illustrated, a wellbore 102 may extend from a wellhead 104 into a subterranean formation 106 from a surface 108. Generally, wellbore 102 may include horizontal, vertical, slanted, curved, and other types of wellbore geometries and orientations. Wellbore 102 may be cased or uncased. In examples, a drill string 110 may begin at wellhead 104 and traverse wellbore 102. A drill bit 112 may be attached to the distal end of the drill string 110 and may be driven, for example, either by a downhole motor and/or via rotation of the drill string 110 from the surface 108. As the drill bit 112 rotates, it extends wellbore 102 into subterranean formation 106. Drill bit 112 may be a part of bottomhole assembly 114 of drilling system 100. While not illustrated, bottomhole assembly 114 may further comprise one or more of a mud motor, power module, steering module, telemetry subassembly, and/or other sensors and instrumentation as will be appreciated by those of ordinary skill in the art. As will be appreciated by those of ordinary skill in the art, bottomhole assembly 114 may be a measurement-while drilling or logging-while-drilling system.

Without limitation, drilling system 100 may comprise an EM induction tool 116. EM induction tool 116 may be a part of bottomhole assembly 114 of drilling system 100. EM induction tool 116 may further comprise a transmitter 118 and a receiver 120. While only a single transmitter 118 and a single receiver 120 are shown on FIG. 1, it should be understood that EM induction tool 116 may comprise more than one transmitter 118 and more than one receiver 120 as desired for a particular application. As disclosed, the concepts that are described herein are valid for any type of transmitter and receiver antenna. As an example, wire antenna, toroidal antenna and/or azimuthal button electrodes, transmitter coils, and/or receiver coils may also be used in the place of the transmitter 118 and/or the receiver 120. EM induction tool 116 may further comprise a tubular 122. Transmitter 118 and receiver 120 may be coupled to or otherwise incorporated into tubular 122. Without limitation, tubular 122 may comprise a drill collar or other suitable tubular component of bottomhole assembly 114. In other applications, as will be discussed below, tubular 122 may include well tubulars, such as a mandrel or casing joint, for example. From utilization of transmitter 118 and/or receiver 120, azimuthal currents may be disposed within the EM induction tool 116. In examples, tubular 122 may be insulated to minimize the azimuthal currents on the EM induction tool 116, thus reducing the direct signal between transmitter 118 and receiver 120.

In operation, transmitter 118 may be used to introduce a current into subterranean formation 106. The current from transmitter 118 may in turn induce a current in nearby conductors. The nearby conductors may be considered the "target" and may include, without limitation, a second wellbore, formation inhomogeneity, a bed boundary and/or an approaching flood front (e.g., water/carbon dioxide front). For example, the second wellbore may include a conductive pipe string, such as wellbore casing, in which an eddy current may be induced by the current from transmitter 118. This eddy current may radiate from the second wellbore. The eddy current induced in the nearby conductors may induce voltages in the receiver 120 that may be recorded and transmitted to surface 108. Using these measurements of the eddy current from the receiver 120, a number of determinations may be made, including, without limitation, formation properties (e.g., resistivity), second wellbore location, wellbore position with respect to a surface point, properties of fluids in the borehole (e.g. resistivity, dielectric constant), casing property (e.g. thickness, magnetic permeability, conductivity) and/or flood front shape and location. While not illustrated, the EM induction tool 116 may include one or more additional components, such as analog-to-digital converter, amplifier, and microprocessor, among others, that may be used to process the measurements from receiver 120 before they may be transmitted to surface 108. Alternatively, raw measurements from receiver 120 may be transmitted to surface 108.

Any suitable technique may be used for transmitting signals from receiver 120 to surface 108, including, but not limited to, mud-pulse telemetry, acoustic telemetry, and electromagnetic telemetry. While not illustrated, bottomhole assembly 114 may include a telemetry subassembly that can transmit telemetry data to the surface. Without limitation, a transmitter in the telemetry subassembly may be operable to generate pressure pulses in the drilling fluid that propagate along the fluid stream to surface 108. At surface 108, pressure transducers (not shown) may convert the pressure signal into electrical signals for a digitizer 124.

Digitizer 124 may supply a digital form of the telemetry signals to an information handling system 126 via a communication link 128, which may be a wired or wireless link. The telemetry data may be analyzed and processed by information handling system 126. For example, the telemetry data could be processed to determine formation properties (e.g., resistivity), second wellbore location, and/or flood front location. With the second wellbore location, a driller could control the bottomhole assembly 114 to intentionally intersect the second wellbore, avoid the second wellbore, and/or drill wellbore 102 in a path parallel to second wellbore. For purposes of this disclosure, information handling system 126 may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, information handling system 126 may be a personal computer, a network storage device, or any other suitable device and may vary in size, shape, performance, functionality, and price. Information handling system 126 may include random access memory (RAM), one or more processing resources such as a central processing unit (CPU) or hardware or software control logic, ROM, and/or other types of nonvolatile memory. Additional components of information handling system 126 may include one or more disk drives, one or more network ports for communication with external devices as well as various input and output (I/O) devices, such as a keyboard, a mouse, and a video display. Information handling system 126 may also include one or more buses operable to transmit communications between the various hardware components.

Figure 2:
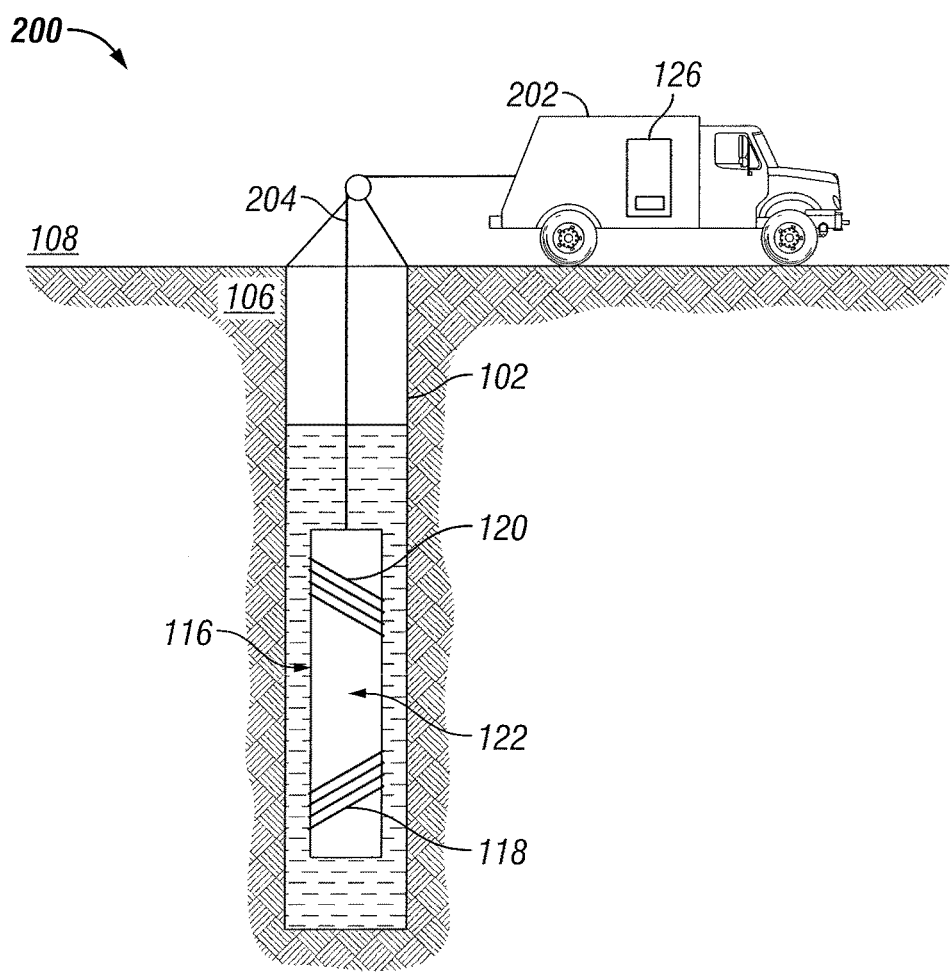
FIG. 2 is an example of a wireline system that includes an EM induction tool.

Without limitation, EM induction tool 116 may be incorporated into a wireline tool. FIG. 2 illustrates an example of a wireline system 200. Wireline system 200 may comprise a recovery vehicle 202, wireline 204, and/or EM induction tool 116. Recovery vehicle 202 may be disposed at surface 108 of wellbore 102. Recovery vehicle 202 may include a spool (not shown) for raising and lowering wireline 204 in wellbore 102. As illustrated, EM induction tool 116 may be coupled to wireline 204, for example, at a distal end of wireline 204. EM induction tool 116 may include transmitter 118 and receiver 120. As previously described, transmitter 118 and receiver 120 may be coupled to tubular 122, which may comprise a mandrel or other suitable tubular. In examples, tubular 122 may be insulated to minimize the azimuthal currents on EM induction tool 116, thus reducing the direct signal between transmitter 118 and receiver 120. Signals from receiver 120 may be transmitted to an information handling system 126, which may be disposed on recovery vehicle 202, for example. It should be understood that other types of wireline systems may be employed, including those in which the wireline is disposed from a spool that is installed at surface 108 instead of being located on a recovery vehicle 202. Specific information about subterranean formation 106, such as resistivity, may be inferred from analysis of the signal from receiver 120. In certain examples, a wireline log may be developed from the signal that includes information about subterranean formation 106, such as formation resistivity.

Figure 3:
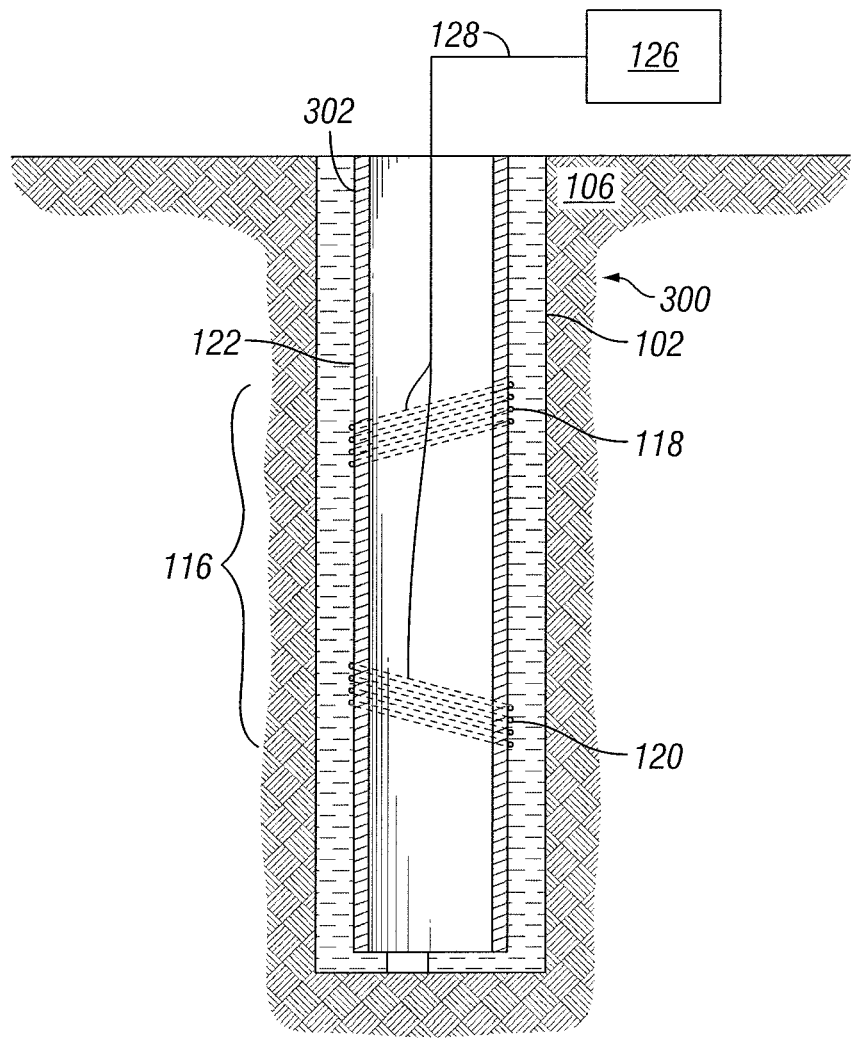
FIG. 3 is an example of a well monitoring system that includes an EM induction tool.

FIG. 3 illustrates an example of a permanent monitoring system 300 in which EM induction tool 116 has been incorporated. As will be appreciated, permanent monitoring system 300 may be used to monitor formation properties, including approaching flood fronts (not illustrated). In examples, permanent monitoring system 300 may comprise a casing 302 disposed within wellbore 102 penetrating subterranean formation 106. Permanent monitoring system 300 may also comprise EM induction tool 116, which may comprise transmitter 118 and receiver 120. As previously described, transmitter 118 and receiver 120 may be coupled to tubular 122. As illustrated, tubular 122 may be section of casing 302, such as one or more casing joints or the like. In examples, tubular 122 may be insulated to minimize the azimuthal currents on EM induction tool 116, thus reducing the direct signal between transmitter 118 and receiver 120. Information handling system 126 may connect to transmitter 118 and/or receiver 120 through communication link 128. Signals from receiver 120 may be transmitted to information handling system 126 by way of communication link 128. Specific information about subterranean formation 106, such as resistivity, approaching flood front, etc., may be inferred from analysis of the signal from receiver 120.

Figure 4:
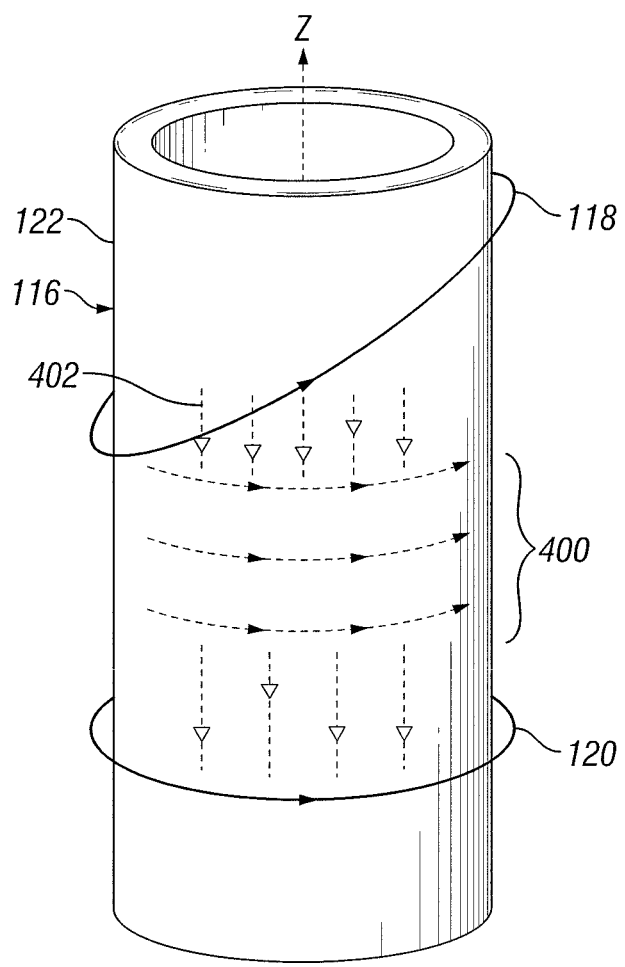
FIG. 4 illustrates example flow of azimuthal currents on a tubular.

During downhole operations in which EM induction tool 116 may be utilized, an azimuthal current may be present within areas in which transmitters 118 and/or receivers 120 may be disposed. Azimuthal currents may be especially pronounced when transmitter 118 and/or receiver 120 are coaxial. As illustrated in FIG. 4, azimuthal currents and axial currents may be induced on EM induction tool 116. The azimuthal currents are generally indicated by circumferential lines 400 and the axial current are general indicated by axial lines 402. EM induction tool 116 may comprise transmitter 118 and receiver 120, which may be spaced axially on tubular 122 along its central or z-axis. In some examples, transmitter 118 and/or receiver 120 may be tilted at an angle, for example of about forty-five degrees. It should be noted that the tilt of transmitter 118 may be adjusted by the operator, depending on the downhole conditions and/or operating parameters.

Figure 5A:
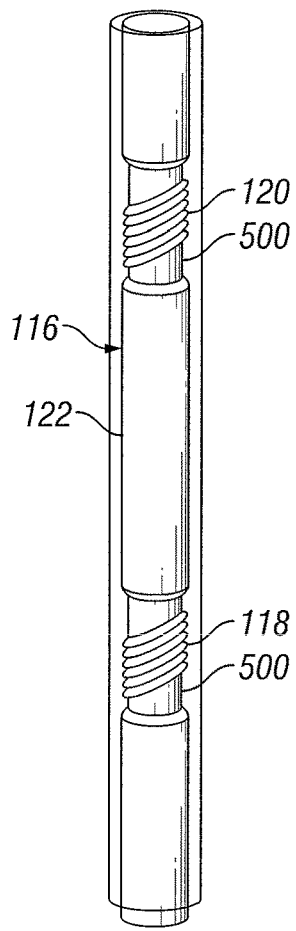
FIGS. 5a and 5b are example receiver orientations on a tubular.
Figure 5B:
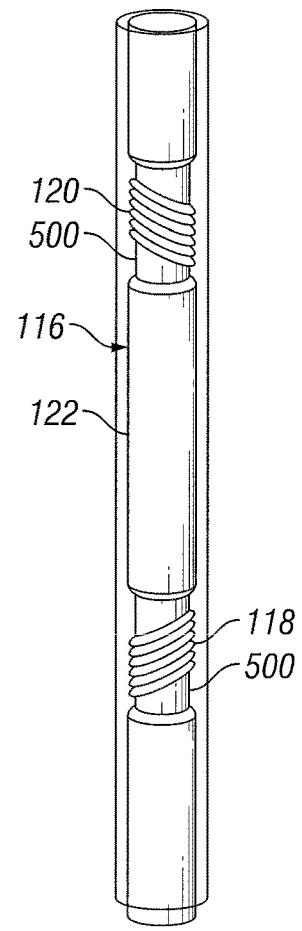

FIGS. 5a and 5b illustrate transmitter 118 and receiver 120 disposed on tubular 122 of EM induction tool 116. In embodiments, EM induction tool 116 may comprise a mixture of transmitters 118 and/or receivers 120. Transmitter 118 and/or receiver 120 may be disposed adjacent ferrite sleeves 500. Ferrite sleeves 500 may enhance the magnetic field and may be disposed between transmitter 118 and/or receiver 120 and EM induction tool 116. In FIGS. 5a and 5b, the separation between transmitter 118 and receiver 120 may vary between about two feet and one hundred feet. Additionally, transmitter-receiver separation on the EM induction tool 116 may be optimized for on a particular application. Without limitation, transmitter-receiver separation may range from about one foot to about two hundred feet. Additionally, FIGS. 5a and 5b illustrate different configurations of the EM induction tool 116 in regards to azimuthal orientation of transmitter 118 and receiver 120. In FIG. 5a, the magnetic moment orientation of receiver 120 may be parallel to the magnetic moment orientation of transmitter 118. In FIG. 5b, the magnetic moment orientation of receiver 120 may be rotated about one hundred and eighty degrees azimuthally from FIG. 5a, which indicates that the magnetic moment of receiver 120 may be at a ninety degree angle to transmitter 118.

Without limitation, receivers 120 may be tilted to an angle chosen by the operator. Tilt of transmitter 118 and/or receiver 120 may be measured from a line that may horizontally cross EM induction tool 116. Without limitation, transmitter 118 and/or receiver 120 may be tilted at an angle of about ten degrees to about thirty degrees, about twenty degrees to about forty-five degrees, about forty degrees to about fifty degrees, about fifty degrees to about sixty degrees, about sixty degrees to about seventy degrees, or about seventy degrees to about eighty degrees.

Figure 6A:
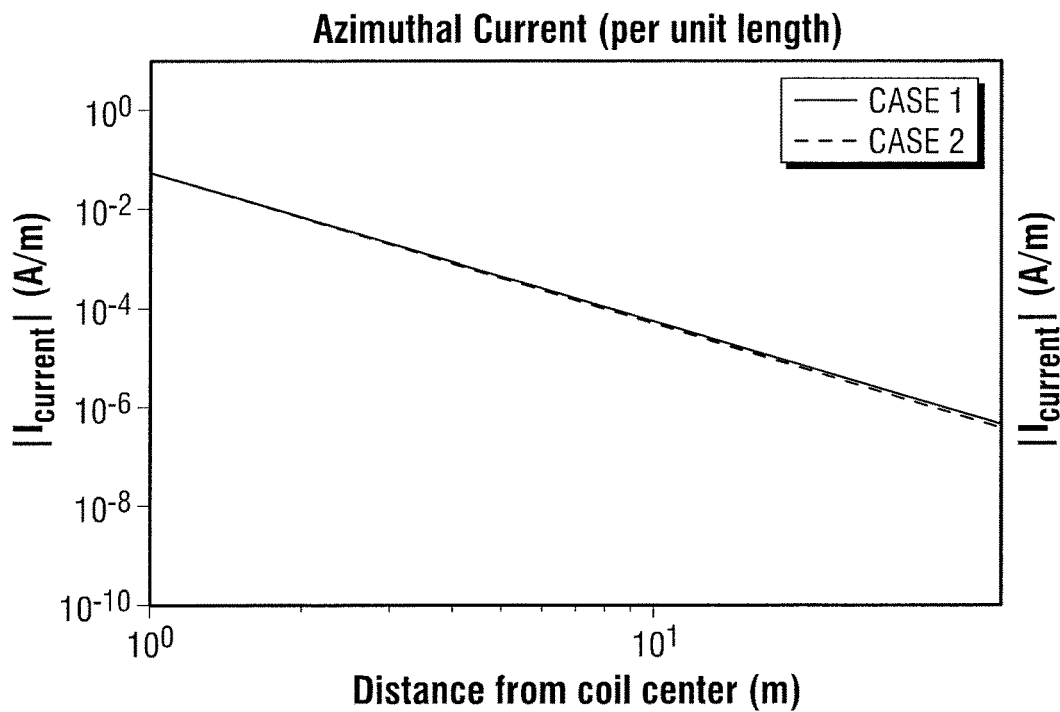
FIG. 6a is an example chart of azimuthal current per unit length induced in a tubular.
Figure 6B:
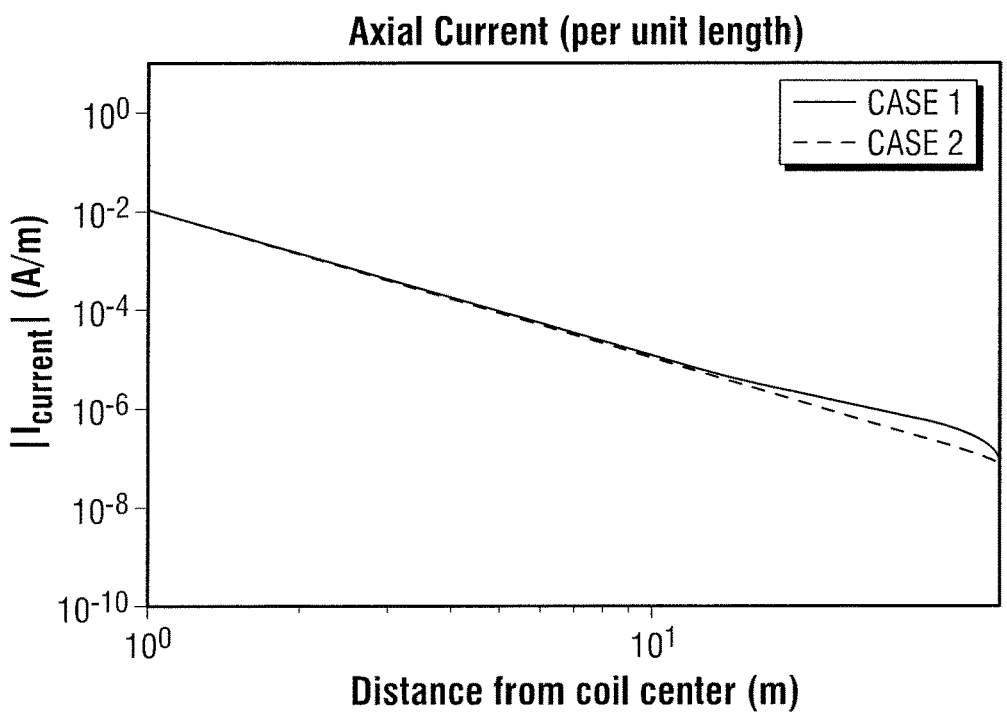
FIG. 6b is an example chart of axial current per unit length induced on a tubular.

FIG. 6a is a chart showing the azimuthal current induced on a tubular 122 by a transmitter 118 tilted at forty-five degrees. In FIG. 6a, the distance from the center of transmitter 118 is plotted versus azimuthal current intensity. FIG. 6b is a chart showing the axial current induced on a tubular 122 by a transmitter 118 tilted at forty-five degree. In FIG. 6b, the distance from the center of transmitter 118 is plotted versus axial current intensity. Both graphs in FIGS. 6a and 6b plot current with a frequency f 1 kHz for two different formation resistivities, represented by the labels 'Case 1' and 'Case 2' A comparison of the graphs in FIGS. 6a and 6b show that the azimuthal current may be dominant from about one meter to about fifteen meters. In both Case 1 and Case 2, the azimuthal current densities, referring to FIG. 6a, may be found to be almost one order of magnitude larger than their axial counterparts, as shown in FIG. 6b. The importance of azimuthal current may be understood by computing the voltage produced at the receiver 120 in the configurations shown in FIG. 5a and FIG. 5b, and comparing these two voltages. The transmitter-receiver spacing in these figures may be about two feet to about one hundred feet. The receiver voltage may computed for the configuration of FIG. 5a in which the magnetic moment of receiver 120 may be parallel to that of the transmitter 118 (referred to in Table 1 below as Receiver Orientation 1) and also for the configuration of FIG. 5b in the receiver 120 has been rotated one hundred and eighty degrees azimuthally so that its magnetic moment makes a ninety degree angle with the transmitter 118 (referred to in Table 1 below as Receiver Orientation 2). One voltage computation may be done with the tubular 122, mud, and ferrite sleeves 500 in place and another voltage computation may be done without the tubular 122. The difference between the two voltages may be the contribution of tubular currents on the received voltages. The computed voltages are provided in Table 1 below:

TABLE 1

| | | Coupling Voltage (Volts) |
|---|---|---|
| Receiver Orientation 1 | Computation 1: Coils and Sleeves Only | 1.95E−07 |
| | Computation 2: Plus Tubular | 3.78E−05 |
| Receiver Orientation 2 | Computation 1: Coils and Sleeves Only | 3.90E−07 |
| | Computation 2: Plus Tubular | 3.76E−05 |

Table 1 illustrates that the tubular currents (represented by the differences between Computation 1 and Computation 2) may contribute to the received voltage at receiver 120. A comparison of Computations 1 and 2 for Receiver Orientation 1 shows that the tubular currents have a significant contribution to the received voltage (e.g., an almost 200 times increase). This is also true for Receiver Orientation 2 where Computations 1 and 2 differ by almost 100 times. The relative importance of azimuthal currents compared to axial currents may be seen upon comparing Computation 2 for the different receiver orientations. It should be noted that the contribution of the azimuthal currents on the received voltage may be the same in both receiver orientations. However, the contribution of the axial current may be positive in Receiver Orientation 1 and may be negative in Receiver Orientation 2. As Computation 2 for both receiver orientations is comparable, it indicates that the axial current has little impact on the received voltage. Almost all of the tubular effect on the received voltage may be considered to come from the azimuthal currents on the tubular.

Accordingly, azimuthal currents may be a significant contributor to a direct signal recorded at receiver 120. Referring to FIG. 4, illustrates azimuthal current 400 may traverse the circumference of tubular 122, which may follow the current flow of transmitters 118 and/or receivers 120. Additionally, mutual inductance may allow for the production of a strong electromotive force at receivers 120. The electromotive force, due to azimuthal current, at receiver 120 may overshadow a desired signal coming from a target well (not illustrated). Devices and methods disclosed herein may be utilized to limit, if not prevent, the azimuthal current. By way of example, tubular 122 may be used to minimize the azimuthal currents on EM induction tool 116, thus reducing the direct signal between transmitter 118 and receiver 120. FIGS. 7-11 describe different embodiments of tubular 122 that may be used for minimizing azimuthal currents on EM induction tool 116.

Figure 7A:
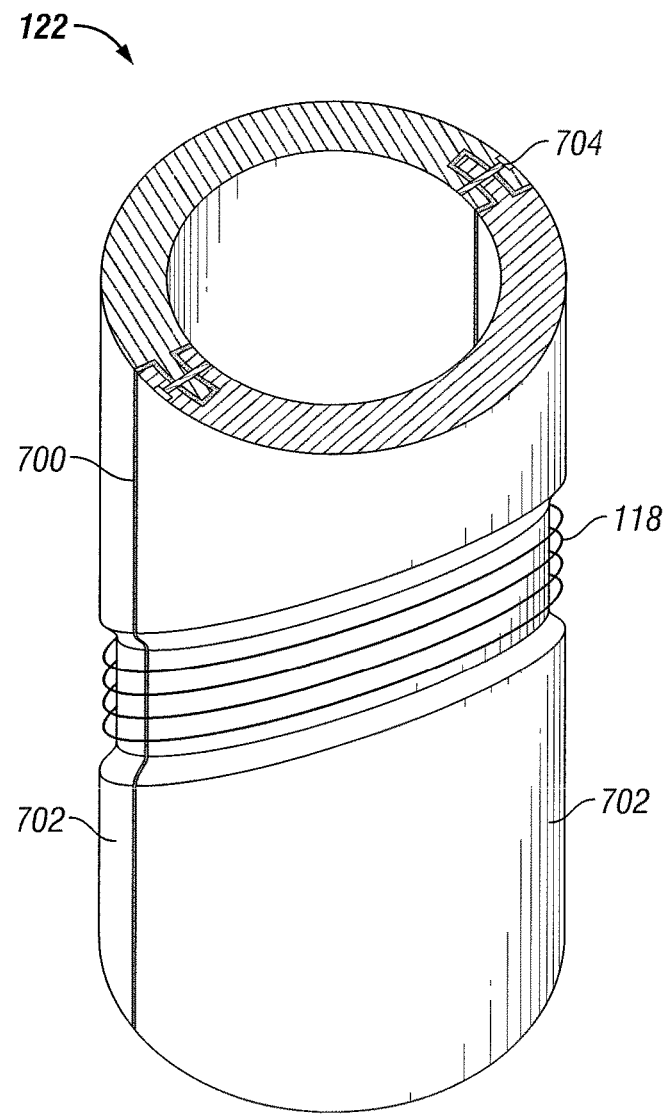
FIGS. 7a-7c illustrate an example of a tubular of an EM induction tool.
Figure 7B:
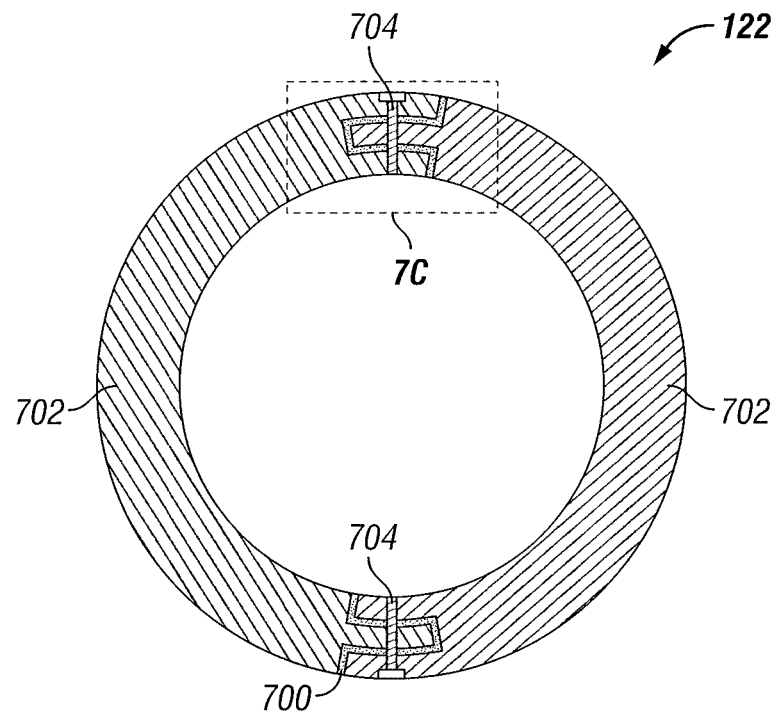
Figure 7C:
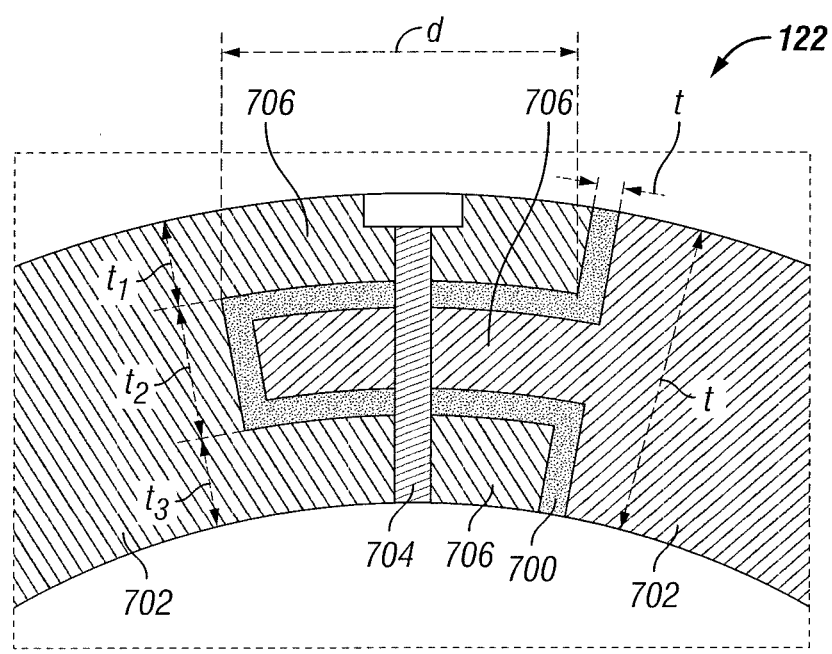

As illustrated in FIGS. 7a to 7c, tubular 122 may be configured to at least partially prevent azimuthal currents produced by transmitters 118 and/or receivers 120. FIG. 7c is a close-up view of the portion of tubular 122, as indicated on FIG. 7b. In examples, tubular 122 may comprise an insulating layer, which may comprise an insulating gap 700, disposed between axial sections 702. Without limitation, insulating gap 700 may comprise a suitable insulating material, such as plastic, epoxy, and/or ceramic. Composite layers of insulating gap 700 may be formed by wetting fiberglass sheets with resin and/or loading an epoxy solution with ceramic particles. Thus, the dielectric strength of the cured material may be sufficiently large to prevent capacitive coupling between different axial sections 702, which may be a problem with high frequencies. Additionally, insulating gap 700 may have strong adhesive properties, which may help hold axial sections 702 together. Axial sections 702 of tubular 122 may fit together along axial grooves, which may traverse the length of tubular 122. Additionally, more than one axial section 702 of tubular 122 may be joined together, which may increase the ability of tubular 122 from preventing azimuthal currents. Axial sections 702 may be held together by a plurality of fasteners 704, which may be bolts, for example. In examples, fasteners 704 may comprise non-conducting material, but may be metallic in order to withstand high mechanical stresses. Fasteners 704 which may comprise metallic elements may form a conductive path between two axial sections 702, but the surface area of the path created may be significantly smaller than that of the boundary formed by insulating gap 700. Without limitation, fasteners 704 may be disposed in any along axial sections 702 in any configuration which may provide strength to tubular 122 and hold axial sections 702 together. Additionally, in examples, axial sections 702 may not require fasteners 704 to be held together, due to mechanical tolerances in the machining process.

As best seen in the cross-sectional views of FIGS. 7b and 7c, axial sections 702 may connect in a tongue and groove connection. With specific reference to FIG. 7c, tubular 122 may have a thickness of t. The thickness of flanges 706 on each of axial sections 702 may be represented by $t_1$, $t_2$, and $t_3$, the thickness of insulating layer 40 may be represented by $t_l$, and the depth of groove may be represented by d. Without limitation, the depth d of the groove may be between t/2 and 3t, and the thicknesses $t_1$, $t_2$, and $t_3$ of the flanges may be between t/5 and t/2. In examples, insulating gap 700 may have a thickness t, between t/1000 and t/10. It should be understood that these ranges are merely exemplary and dimensions outside these specific ranges may be suitable for particular applications.

Figure 8A:
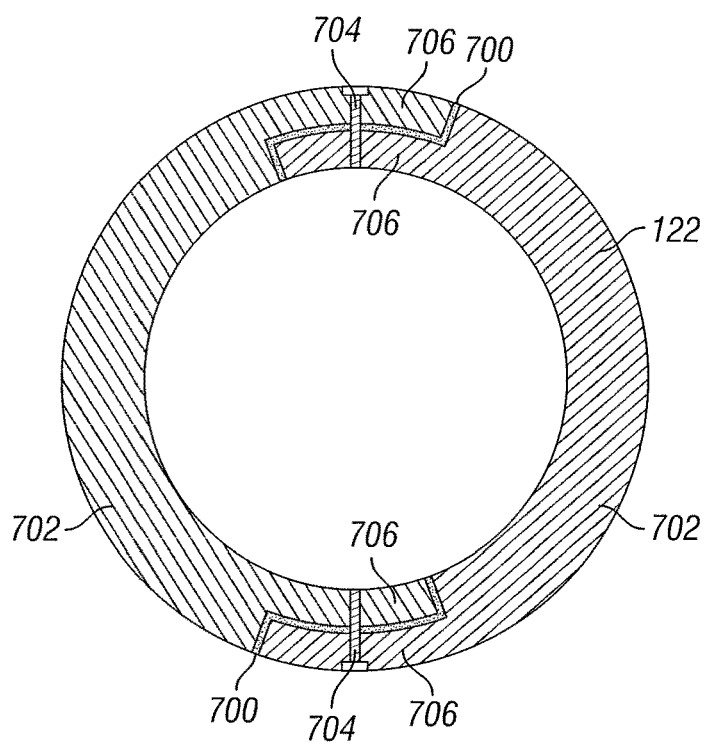
FIGS. 8a-8c illustrate different example arrangements of an insulating layer in a tubular of an EM induction tool.
Figure 8B:
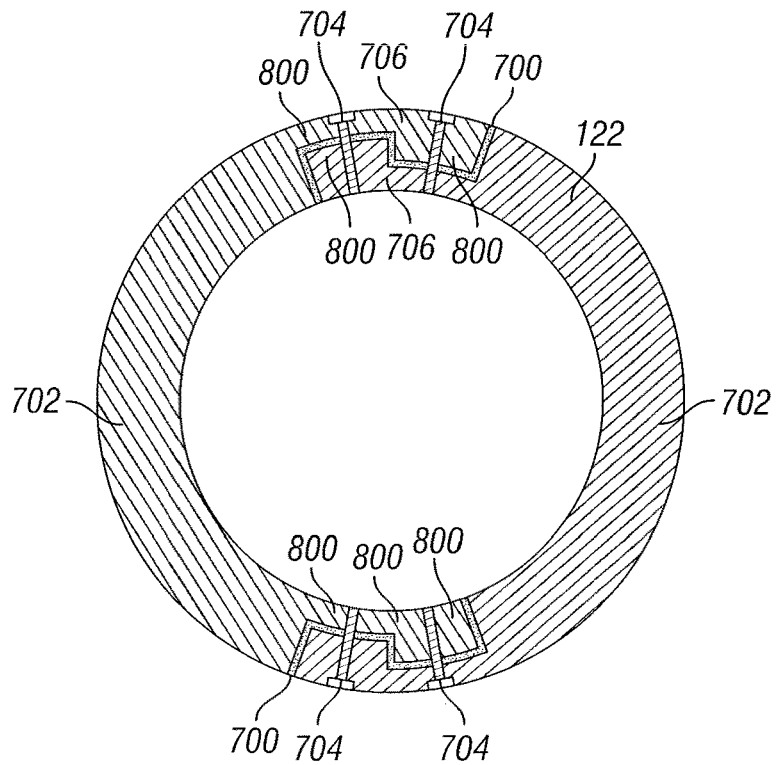
Figure 8C:
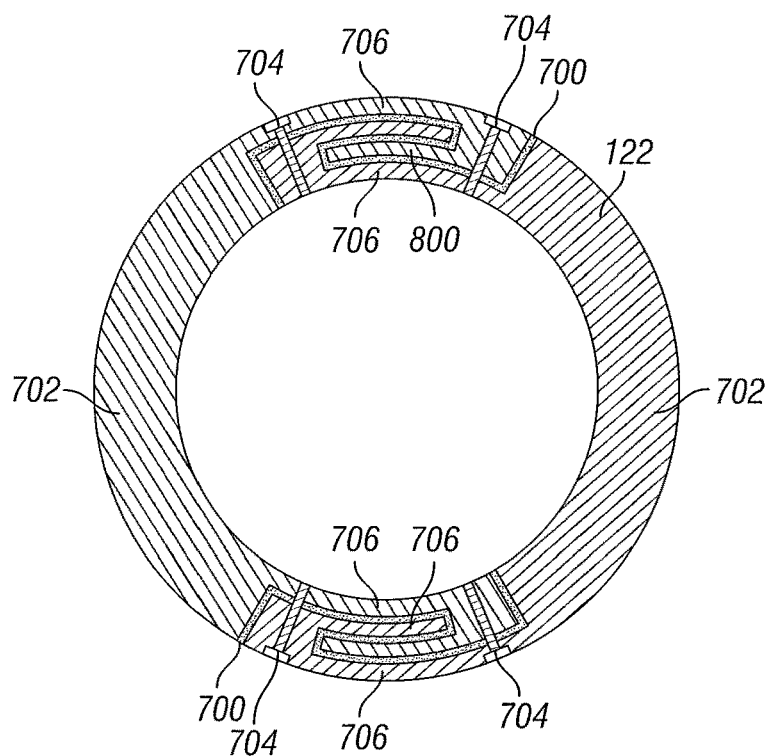

FIGS. 8a-8c illustrate different examples of arrangements of tubular 122 in which axial sections 702 may be separated by insulating gap 700 and held together by fasteners 704. In each of these examples, the insulating gap 700 may be an insulating gap and non-azimuthally symmetric. With respect to FIG. 8a, the axial sections 702 may be connected by overlapping flanges 706 bolted to one another. Without limitation, the thickness $t_1$, $t_2$ of flanges 706 in FIG. 8a may be between t/4 and 3t/4, wherein t is the thickness of tubular 122. With respect to FIG. 8b, the axial sections 702 may be connected by flanges 706 that overlap and are fastened to one another with fasteners 704, wherein the overlapping flanges 706 each include an enlarged end 800. Without limitation, the thickness $t_1$, $t_3$ of flanges 706 and the thickness $t_2$ of enlarged end in FIG. 8b may be between t/5 and 4t/5, wherein t is the thickness of insulated tubular. With respect to FIG. 8c, the axial sections 702 may be connected by flanges 706 that interlock and are fastened to one another with fasteners. Without limitation, thicknesses $t_1$, $t_2$, $t_3$, and $t_4$ of flanges 706 on FIG. 8c may be between (t/6) and (5t/6). In each example of FIGS. 8a-8c, the connections formed between the axial sections 702 may have separate resilience characteristics against axial, azimuthal, and radial stress. In examples, not illustrated, tubular 122 may be divided into axial sections 702 by straight axial lines, which may be filled with insulating gap 700 and held together by fastener 704. This example may remove the need for tongue-and-groove, overlapping, and/or interlocking connections.

While various placements of fasteners 704 are illustrated in FIGS. 8a-8c, it should be understood that the specific placement and number of fasteners 704 should be limited to what is shown. By way of example, the axial and azimuthal spacing between fasteners 704 can vary as will be appreciated by those of ordinary skill in the art.

Figure 9:
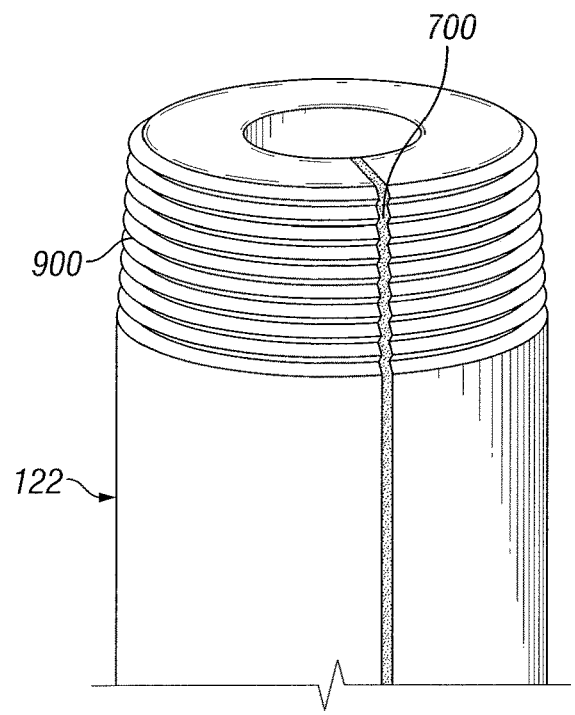
FIG. 9 illustrates an example of an insulating layer in a threaded end of a tubular of an EM induction tool.

FIG. 9 illustrates another example of tubular 122. As illustrated, insulating gap 700 may traverse threading 900, which may be on one end of tubular 122. Without limitation, threading 900 may be used to connect tubular 122 to an adjacent tubular (not shown). By having insulating gap 700 traverse threading 900, azimuthal current may not overcome insulating gap 700 by moving around the top and/or bottom of insulating gap 700. Without limitation, traversing the entire length of tubular 122 may allow insulating gap 700 to prevent nearly all azimuthal current.

Figure 10:
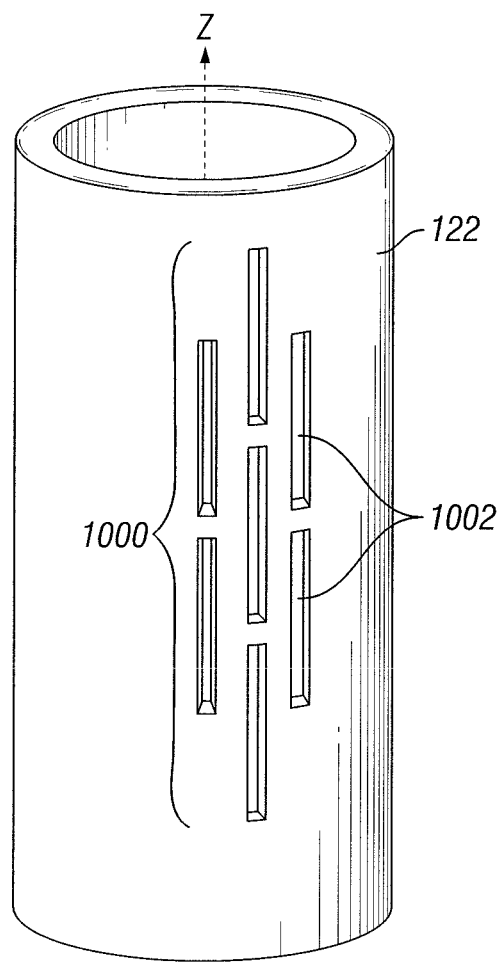
FIG. 10 illustrates an example of an insulating layer that comprises slots disposed in the tubular of an EM induction tool.

In examples, as illustrated in FIG. 10, insulating barrier 1000 may comprise a slot 1002 and/or a plurality of slots 1002 cut out of, or otherwise formed in, tubular 122. As illustrated, the insulating barrier 1000 may be an insulation gap and non-azimuthally symmetric. As illustrated, slots 1002 may extend vertically in tubular 122 in that slots 1002 may extend generally parallel to the z-axis of tubular 122. The specific spacing and size of slots 1002 may vary as desired for a particular application. In examples, slots 1002 may be about eight inches to about sixteen inches long and may be about a ¹⁄₃₂ of an inch to about three inches wide. Transmitters 118 (not illustrated) and receivers 120 (not illustrated) may be disposed near and/or adjacent insulating barrier 1000. In this example, slots 1002 may prevent movement of azimuthal currents around tubular 122 by creating physical gaps within tubular 122. Each slot may remove all the metal between the outer surface and inner surface of tubular 122. In examples, slots 1002 may be filled with non-metallic insulation material, such as insulating material, such as plastic, epoxy, and/or ceramic. To maintain structural integrity of tubular 122, slots 1002 may not traverse the length of tubular 122. Without limitation, slots 1002 may be arranged in one or more circumferentially spaced rows (or columns), wherein each row may include one, two, three, or more slots 1002. Without limitation, the rows of slots 1002 may be offset in the circumferential direction to prevent a direct line for azimuthal currents to maneuver through. In other words, in a circumferential direction, the slots 1002 may be alternately located in two respective rows and partially overlapping, as shown in FIG. 10. Without limitation, the slots 1002 may be separated by a ¼ inch to about three inches. This may completely limit that movement of azimuthal current. In examples, slots 1002 may be disposed about a single axis of tubular 122. In additional examples, slots 1002 may be disposed about multiple axes on tubular 122. Slots 1002 may be disposed on about one percent to about five percent of tubular 122, about ten percent to about twenty-five percent of tubular 122, about twenty-five percent to about seventy-five percent of tubular 122, or about fifty percent to one hundred percent of tubular 122. Slots 1002 may further be disposed at an angle to prevent the movement of azimuthal current.

Figure 11:
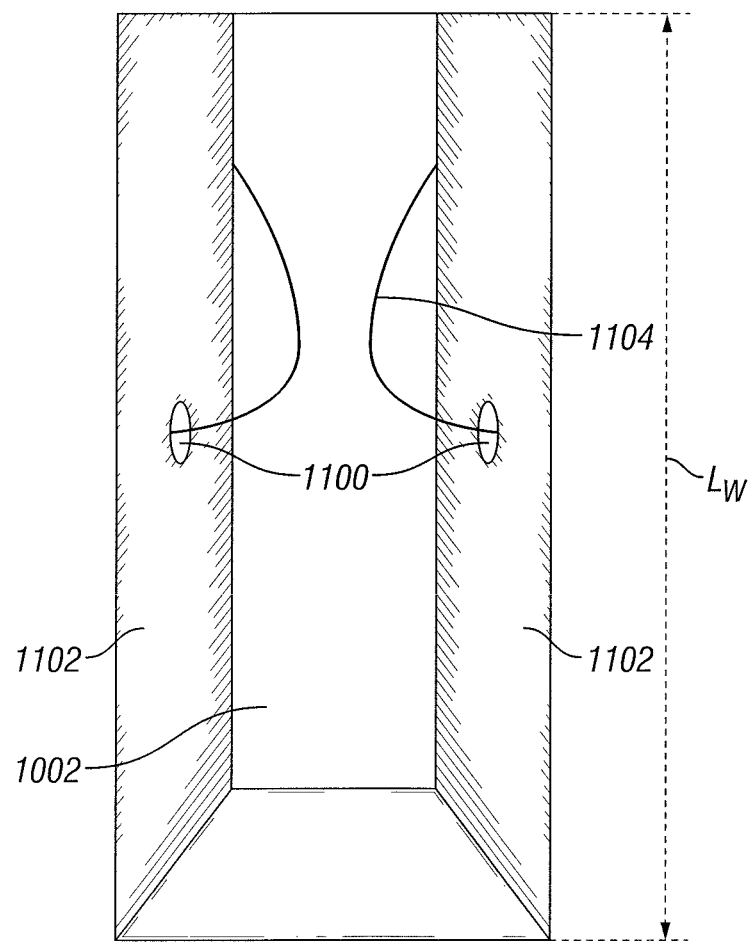
FIG. 11 illustrates use of a slot in a tubular as a transmitter or receiver.

With additional reference to FIG. 11, slot 1002 in tubular 122 may be used as a transmitter 118 and/or receiver 120. As illustrated, terminals 1100 may be disposed in walls 1102 of slot 1002. Terminal 1100 may connect to a winding 1104, which may traverse the outer layer of tubular 122. In examples, there may be a plurality of terminals 1100 and a plurality of windings 1104. Thus, slots 1002 may be utilized for excitation and/or receiving purposes. A voltage may be applied through terminals 1100 to opposite walls 1102 of a slot 1002. The metal within tubular 122 may act as a coil. Transmitter and/or received signals may be enhanced by placing ferrite material (not illustrated) within the slot 1002. In examples, the slot 1002 may be excited along any point of wall 1102, but embodiments may place terminals 1100 are or near a midpoint of wall 1102. Without limitation, the slot length ($L_w$) may be larger than and/or equal to the circumference of tubular 122, which may force more than fifty percent of the induced current around the circumference, rather than the slot perimeter.

Figure 12:
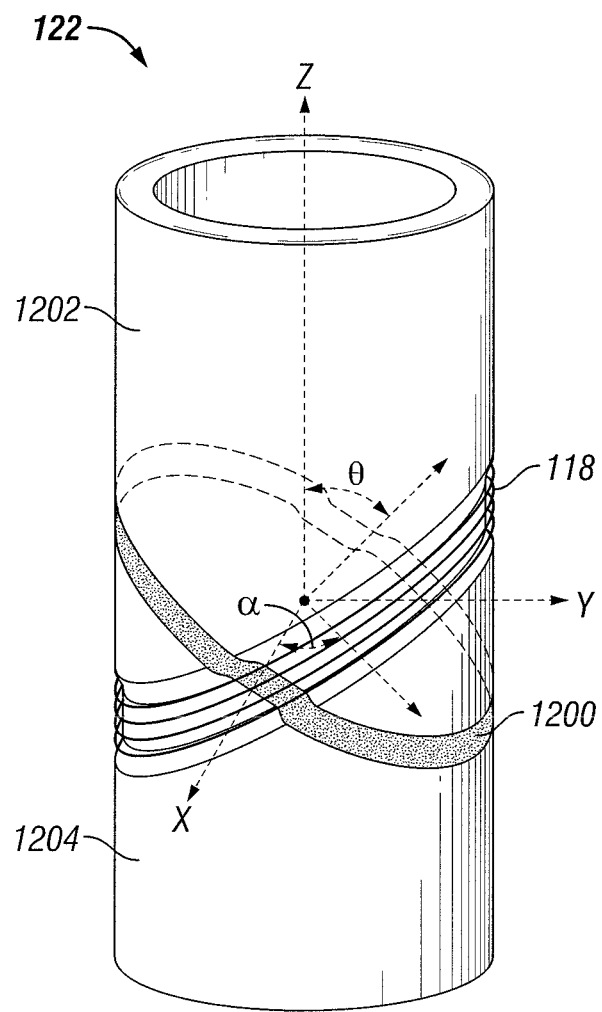
FIG. 12 illustrates an example of an insulating layer in the form of a tilted insulated gap.

Referring now to FIG. 12, an additional example of angled insulating layer 1200 is shown. As illustrated, angled insulating layer 1200 may be disposed at an angle within tubular 122, which may form a tilted insulated layer. In the illustrated embodiment, angled insulating layer 1200 may be insulation gap and non-azimuthally symmetric, where azimuthal symmetry may be defined with respect to axial direction (i.e., z-axis). Angled insulating layer 1200 may be formed from a suitable as insulating material, such as plastic, epoxy, and/or ceramic. Without limitation, insulating tubular 122 may comprise first tubular section 1202 and second tubular section 1204. Angled insulating layer 1200 may be disposed between first tubular section 1202 and second tubular section 1204, coupling the first tubular section 1202 and the second tubular section 1204 together. Any suitable means may be used to couple angled insulating layer 1200 to first tubular section and second tubular section 1204, including threaded connections, for example.

In examples, angled insulating layer 1200 may further comprise transmitter 118. However, it should be noted that receiver 120 (not illustrated) may be used with titled insulated gap as well. Without limitation, azimuthal current may be produced by transmitter 118, which may flow within the area around transmitters 118. Disposing angled insulating layer 1200 at an opposite tilt, as that of transmitter 118, may allow angled insulating layer 1200 to prevent nearly all azimuthal current from traversing around tubular 122. For example, angled insulating layer 1200 may have a tilt angle θ of about ten degrees to about thirty degrees, about twenty degrees to about forty-five degrees, about forty degrees to about fifty degrees, about fifty degrees to about sixty degrees, about sixty degrees to about seventy degrees, or about seventy degrees to about eighty degrees. In further examples, angled insulating layer 1200 may be substantially parallel to a central axis, where substantially parallel may be defined as being about one degree to about five degrees from being actually parallel. In examples, angled insulating layer 1200 may be any suitable thickness. Angled insulating layer 1200 may also be disposed at an azimuthal angle α, which may be greater than 0. However, blocking azimuthal currents may be more dependent on the tilt angle θ so selection of the azimuthal angle α may be arbitrary. Angled insulating layer 1200 may have a thickness as desired for a particular application A suitable thickness may be, but is not limited to, about ½ an inch to about twelve inches, about two inches to about ten inches, about four inches to about eight inches, or about six inches to about twelve inches. Additionally, transmitters 118 may be disposed within a depression of tubular 122 and/or disposed along the outer surface of tubular 122 with no depression. Thus, angled insulating layer 1200 may conform to the outer surface of insulating tubular 122.

Accordingly, this disclosure described systems, tools, and methods that may be used in downhole operations. An EM induction tool may comprise a tubular, which may further comprise a body with a central axis and an insulating layer that may be non-azimuthally symmetric with respect to the central axis, a transmitter coupled to the tubular; and a receiver coupled to the tubular. This EM induction tool may include any of the various features of the systems, tools, and methods disclosed herein. In examples, the body of the EM induction tool may be a casing joint, a mandrel, or a bottomhole assembly. Additionally, the insulating layer of the EM induction tool may be disposed between axial sections of the body. Without limitation the insulating layer may traverse threading on one end of the body. Additionally, the axial sections are connected in a tongue-and-groove connection or may be bolted to one another. The insulating layer of the EM induction tool may have a thickness of between t/1000 to about t/10, wherein t is the thickness of the tubular body. In examples the insulating layer comprises a plurality of slots disposed in the body. Without limitation, the slots may be arranged in staggered rows that are circumferentially spaced. Each of the slots may be about 8 inches to about 16 inches long and about ⅓₂ inch to about 3 inches wide.

The body of the EM induction tool may comprise a first tubular section and a second tubular section, in which the insulating layer may be disposed between the first tubular section and the second tubular section at a tilt angle of about 10 degrees to about 80 degrees, and the insulating layer couples the first tubular section to the second tubular section. Without limitation the insulating layer of the EM induction tool may comprise a plastic, a ceramic, or an epoxy. Additionally, the insulating layer may be substantially parallel to the central axis. In further examples the transmitter of the EM induction tool may be a transmitter coil and the receiver of the EM induction tool may be a receiver coil Without limitation, a method of reducing azimuthal current may be provided, wherein the method may comprise introducing a current through a transmitter into a subterranean formation, in which the transmitter may be coupled to a tubular, allowing an insulating layer of the tubular to at least partially block azimuthal currents originating from the transmitter from flowing on the tubular, in which the insulating layer may be non-azimuthally symmetric, and measuring eddy currents induced by the current with one or more receivers coupled to the tubular. This method may include any of the various features of the systems, methods, and tools disclosed herein. In examples, the body of the EM induction tool may be a casing joint, a mandrel, or a bottomhole assembly. In examples, the tubular may be a bottom assembly, thus the method may further comprise drilling a wellbore with a drill bit disposed on the bottomhole assembly. The method may further comprise lowering the tubular into a wellbore on a wireline, in which the tubular may be a casing string installed in a wellbore. Without limitation, the insulating layer may be disposed between axial sections of the body. In further examples, the insulating layer comprises a plurality of slots disposed in the body. Each of the slots may be about 8 inches to about 16 inches long and about 1/32 inch to about 3 inches wide.

The body within the method of reducing azimuthal current may comprise a first tubular section and a second tubular section, in which the insulating layer may be disposed between the first tubular section and the second tubular section at a tilt angle of about 10 degrees to about 80 degrees, and the insulating layer may couple the first tubular section to the second tubular section. Without limitation, the insulating layer may comprise a plastic, a ceramic, or an epoxy and the insulating layer may be substantially parallel to a central axis of the tubular.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. An electromagnetic induction tool comprising:
    a tubular comprising a body with a central axis and an insulating gap that is non-azimuthally symmetric with respect to the central axis and traverses the entire length of the central axis;
    an insulating layer placed in the insulating gap and the insulating layer is configured to at least partially block azimuthal current from flowing azimuthally on the tubular;
    a transmitter coupled to the tubular; and
    a receiver coupled to the tubular.

2. The tool of claim 1, wherein the body is a casing joint, a mandrel, or a bottomhole assembly.

3. The tool of claim 1, wherein the insulating layer is disposed between axial sections of the body.

4. The tool of claim 3, wherein the insulating layer traverses threading on one end of the body.

5. The tool of claim 3, wherein the axial sections are connected in a tongue-and-groove connection.

6. The tool of claim 3, wherein the axial sections are bolted to one another.

7. The tool of claim 1, wherein the insulating layer has a thickness of between t/1000 to about t/10, wherein t is the thickness of the tubular.

8. The tool of claim 1, wherein the body comprises a first tubular section and a second tubular section, wherein the insulating layer is disposed between the first tubular section and the second tubular section at a tilt angle of about 10 degrees to about 80 degrees, wherein the insulating layer couples the first tubular section to the second tubular section.

9. The tool of claim 1, wherein the insulating layer comprises a plastic, a ceramic, or an epoxy.

10. The tool of claim 1, wherein the insulating layer is substantially parallel to the central axis.

11. The tool of claim 1, wherein the transmitter is a transmitter coil, and wherein the receiver is a receiver coil.

12. A method of reducing azimuthal current, comprising:
    introducing a current through a transmitter into a subterranean formation, wherein the transmitter is coupled to a tubular comprising:
        an insulating gap that is non-azimuthally symmetric with respect to a central axis of the tubular; and
        an insulating layer placed in the insulating gap;
    allowing an insulating layer of the tubular to at least partially block azimuthal currents originating from the transmitter from flowing on the tubular, wherein the insulating layer is non-azimuthally symmetric; and measuring eddy currents induced by the current with one or more receivers coupled to the tubular.

13. The method of claim 12, wherein the tubular is a bottom assembly, the method further comprising drilling a wellbore with a drill bit disposed on the bottomhole assembly.

14. The method of claim 12, further comprising lowering the tubular into a wellbore on a wireline.

15. The method of claim 12, wherein the tubular is a casing string installed in a wellbore.

16. The method of claim 12, wherein the insulating layer is disposed between axial sections of the body.

17. The method of claim 12, wherein the insulating layer comprises a plurality of slots disposed in the body.

18. The method of claim 12, wherein the body comprises a first tubular section and a second tubular section, wherein the insulating layer is disposed between the first tubular section and the second tubular section at a tilt angle of about 10 degrees to about 80 degrees, wherein the insulating layer couples the first tubular section to the second tubular section.

19. The method of claim 12, wherein the insulating layer comprises a plastic, a ceramic, or an epoxy.

20. The method of claim 12, wherein the insulating layer is substantially parallel to a central axis of the tubular.

21. An electromagnetic induction tool comprising:
a tubular comprising a body with a central axis;
a plurality of slots disposed in the body and are non-azimuthally symmetric with respect to the central axis, arranged in staggered rows that are circumferentially spaced, and the plurality of slots are configured to at least partially block azimuthal current from flowing azimuthally on the tubular;
a transmitter coupled to the tubular; and
a receiver coupled to the tubular.

22. The tool of claim 21, wherein each of the slots are about 8 inches to about 16 inches long and about $\frac{1}{32}$ inch to about 3 inches wide.

* * * * *